(12) United States Patent
Mano

(10) Patent No.: US 9,737,283 B2
(45) Date of Patent: Aug. 22, 2017

(54) ULTRASOUND MEASUREMENT APPARATUS AND ULTRASOUND MEASUREMENT METHOD

(71) Applicant: SEIKO EPSON CORPORATION, Tokyo (JP)

(72) Inventor: Tomonori Mano, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 222 days.

(21) Appl. No.: 14/281,095

(22) Filed: May 19, 2014

(65) Prior Publication Data

US 2014/0364740 A1    Dec. 11, 2014

(30) Foreign Application Priority Data

Jun. 6, 2013   (JP) ................................ 2013-119570

(51) Int. Cl.
*A61B 8/08*   (2006.01)

(52) U.S. Cl.
CPC .......... *A61B 8/0891* (2013.01); *A61B 8/0858* (2013.01); *A61B 8/5223* (2013.01)

(58) Field of Classification Search
CPC ..... A61B 5/02007; A61B 5/022; A61B 5/489; A61B 5/721; A61B 8/5223; A61B 2019/461; A61B 8/0891; A61B 8/0858; G01S 15/8979; G01S 15/8984; G01S 7/52036; G01S 7/52042; G06T 2007/10132; G06T 2207/30101; G06T 7/0085

See application file for complete search history.

(56) References Cited

U.S. PATENT DOCUMENTS 6,132,373 A     10/2000   Ito et al.
2010/0063391 A1*  3/2010   Kanai ................... A61B 8/08
                                                    600/437

FOREIGN PATENT DOCUMENTS

JP   A-11-318896   11/1999
JP   A-2009-39277   2/2009

* cited by examiner

*Primary Examiner* — Elmer Chao
(74) *Attorney, Agent, or Firm* — Oliff PLC

(57) ABSTRACT

A first interface of a media-adventitia interface and a second interface of a lumen-intima interface are specified on the basis of reflected waveform data in an n-th frame, a first interface of a media-adventitia interface and second interfaces of a lumen-intima interface are specified on the basis of reflected waveform data in an m-th frame, a first interface displacement amount and second interface displacement amounts between the n-th and m-th frames are determined, a reference displacement amount is calculated from the same reflected waveform data by phase difference tracking as the displacement amount of a vascular wall, and evaluation values for evaluating interface specification credibility are calculated from the first interface displacement amount, the second interface displacement amounts, and the reference displacement amount.

5 Claims, 5 Drawing Sheets

FIRST EVALUATION VALUE (EP1) = | dHp − dH1 |

SECOND EVALUATION VALUE (EP2) = | dHp − dH2 |

THIRD EVALUATION VALUE (EP3) = | dHp / dH1 |

FOURTH EVALUATION VALUE (EP4) = | dHp / dH2 |

FIFTH EVALUATION VALUE (EP5) = | dH1 − dH2 | ical Field

The present invention relates to an ultrasound measurement apparatus which has a function of specifying the position of a layer structure of a vascular wall on the basis of a reflected wave signal of an ultrasonic wave irradiated onto a blood vessel, or the like.

2. Related Art

In recent years, an ultrasound measurement apparatus is used to measure or diagnose arteriosclerosis of a blood vessel or a cardiovascular function. For example, in order to diagnose arteriosclerosis, it is necessary to measure the IMT (Intima Media Thickness) of a blood vessel. This is equal to measuring the distance between a lumen-intima interface and a media-adventitia interface of a vascular wall, and measurement precision of these interfaces is essential for appropriate diagnosis of the IMT.

In measuring the distance between the lumen-intima interface and the media-adventitia interface of the vascular wall, for example, an ultrasound probe having an array of a plurality of ultrasound transducers arranged therein is applied to the neck to irradiate an ultrasound beam. Then, a reflected wave signal (RF signal) applied to and reflected from the carotid artery is received by the ultrasound probe, and the reflected wave signal is processed to search a vascular wall.

While the ultrasonic signal is irregularly reflected in a living body, the ultrasonic signal tends to be comparatively strongly reflected at the interface of the lumen and the vascular wall of the blood vessel or the interface between the membranes of the vascular wall. For this reason, for example, a position at which the strength (amplitude) of the reflected wave signal is great is detected by differential processing, threshold value processing, or the like, thereby searching the position of the vascular wall.

However, the reflected wave of the lumen-intima interface has signal strength smaller than the signal strength of the reflected wave of the media-adventitia interface and is likely to be buried in noise. Specifically, an anterior wall (a vascular wall portion on a side close to the ultrasound probe) is likely to be affected by multiple reflection of the ultrasonic wave, and the contour is likely to be blurred. For this reason, it is difficult to stably measure the IMT of the anterior wall or a posterior wall (a vascular wall portion on a side separated from the ultrasound probe).

In connection with this, JP-A-11-318896 discloses a technique which translates the signal strength of the reflected wave to brightness and searches a brightness peak to automatically calculate the value of the IMT. Although a method which searches a brightness peak is difficult to detect the lumen-intima interface for the above-described reason, JP-A-11-318896 discloses a method which complements for this using regression curve correction or the average value of detected positions. However, in this method, when there are many positions which cannot be detected, IMT measurement precision may be degraded and an error to a true value may increase.

To begin with, since the thickness of the vascular wall, the wall composition, or the like differs for every individual, precision or credibility of detecting an interface of a layer structure of a vascular wall from a reflected wave signal of an ultrasonic wave from a living body differs depending on a living body to be measured. Accordingly, even if the IMT is automatically calculated using a known technique, there is a problem in that it is not possible to determine how much credible and stable is the value of the IMT.

SUMMARY

An advantage of some aspects of the invention is to realizes a technique for determining credibility in specifying the position of a layer structure of a vascular wall on the basis of a reflected wave signal of an ultrasonic wave irradiated onto a blood vessel.

A first aspect of the invention is directed to an ultrasound measurement apparatus including a first specification unit which specifies the position of a first interface in a layer structure of a vascular wall of a blood vessel on the basis of a reflected wave signal of an ultrasonic wave irradiated onto the blood vessel, a second specification unit which specifies the position of a second interface in the layer structure of the vascular wall of the blood vessel on the basis of the reflected wave signal, and a credibility determination unit which determines that both or one of the position specified by the first specification unit and the position specified by the second specification unit is a layer of the vascular wall of the blood vessel on the basis of the amount of change of the position specified by the first specification unit and the amount of change of the position specified by the second specification unit.

As another aspect, the first aspect of the invention can be configured as an ultrasound measurement method including executing first specification processing for specifying the position of a first interface in a layer structure of a vascular wall of a blood vessel on the basis of a reflected wave signal of an ultrasonic wave irradiated onto the blood vessel, executing second specification processing for specifying the position of a second interface in the layer structure of the vascular wall of the blood vessel on the basis of the reflected wave signal, and determining that both or one of the position specified by the first specification processing and the position specified by the second specification processing is a layer of the vascular wall of the blood vessel on the basis of the difference between the amount of change of the position specified by the first specification processing and the amount of change of the position specified by the second specification processing.

According to the first and another aspect of the invention, it is possible to specify the position of each of the first interface and the second interface in the layer structure of the vascular wall, and to determine whether or not the specified interface position is the layer of the vascular wall from the amount of change of the position accompanying the pulsation (the pulsation of the heart).

A second aspect of the invention is directed to the ultrasound measurement apparatus according to the first aspect of the invention, wherein the first interface is an interface at which the signal strength of the reflected wave signal appears to be higher than the second interface, and the determination unit determines that the position specified by the second specification unit is a layer of the vascular wall of the blood vessel when the amount of change of the position specified by the second specification unit is close to the amount of change of the position specified by the first specification unit.

Specifically, a third aspect of the invention is directed to the ultrasound measurement apparatus according to the second aspect of the invention, wherein the first specification unit specifies the position of a media-adventitia interface of the blood vessel as the position of the first interface, and the second specification unit specifies the position of a lumen-intima interface of the blood vessel as the position of the second interface.

According to the second and third aspects of the invention, it becomes possible to specify the first interface and the second interface. Accordingly, it is possible to accurately distinguish between the first and second interfaces and to determine the position of the layer of the vascular wall.

A fourth aspect of the invention is directed to the ultrasound measurement apparatus according to the first aspect of the invention, wherein the first specification unit specifies the position of a media-adventitia interface of an anterior wall portion of the blood vessel and the position of a media-adventitia interface of a posterior wall portion of the blood vessel as the position of the first interface, the second specification unit specifies the position of a lumen-intima interface of an anterior wall portion of the blood vessel and the position of a lumen-intima interface of a posterior wall portion of the blood vessel as the position of the second interface, and the determination unit calculates the amount of change of the outer diameter of the blood vessel based on the position of the first interface as the amount of change of the position specified by the first specification unit, calculates the amount of change of the inner diameter of the blood vessel based on the position of the second interface as the amount of change of the position specified by the second specification unit, and determines that the position specified by the second specification unit is a layer of the vascular wall of the blood vessel when the amount of change of the position specified by the second specification unit is close to the amount of change of the position specified by the first specification unit.

According to the fourth aspect of the invention, it is possible to determine the position of the layer of the vascular wall on the basis of the fact that the amount of change of the media-adventitia and the amount of change of the lumen-intima accompanying the pulsation of the blood vessel are the same or substantially the same.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
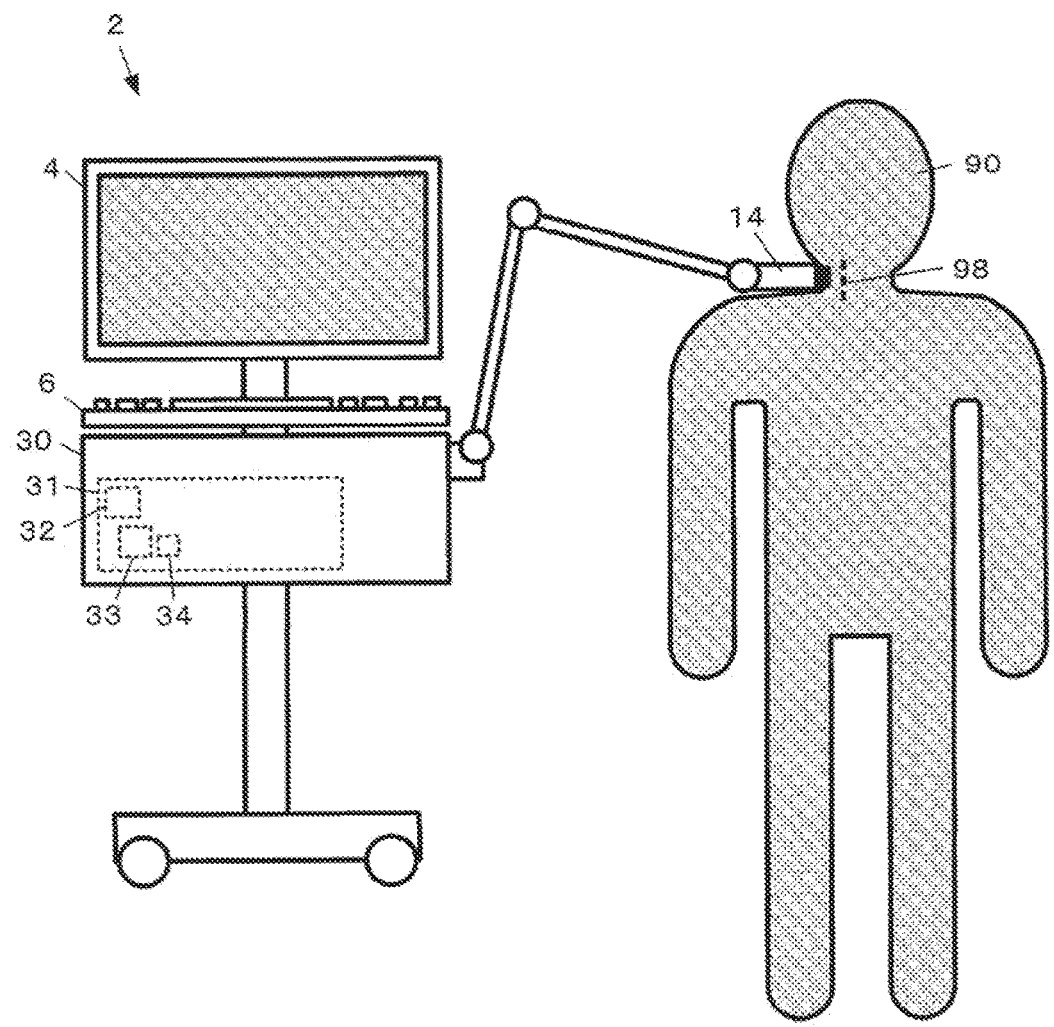
FIG. 1 is a diagram showing a system configuration example of an ultrasound measurement apparatus.

FIG. 1 is a diagram showing a system configuration example of an ultrasound measurement apparatus in this embodiment.

An ultrasound measurement apparatus 2 is an apparatus which measures a reflected wave of an ultrasonic wave to measure biological information of a subject 90. In this embodiment, the position of an interface in a wall portion layer structure of a blood vessel 98 is measured, and an IMT (Intima Media Thickness) is calculated as biological information from the measurement result.

The ultrasound measurement apparatus 2 includes a touch panel 4 which doubles as a unit for displaying a measurement result or operation information in the form of images and a unit for operation input, a keyboard 6 for operation input, an ultrasound probe 14, and a processing device 30. A control board 31 is mounted in the processing device 30, and is connected to perform signal transmission and reception with the respective units, such as the touch panel 4, the keyboard 6, and the ultrasound probe 14.

On the control board 31, in addition to a CPU 32, an ASIC, and various LSIs, a storage medium 33, such as an IC memory or a hard disk, and a communication IC 34 which realizes data communication with an external apparatus are mounted. The processing device 30 executes a measurement program stored in the storage medium 33 on the CPU 32 or the like, and executes transmission control of an ultrasonic wave from the ultrasound probe 14, reception control of a reflected wave of an ultrasonic wave, signal analysis, and the like. Furthermore, the processing device 30 realizes functions, such as arithmetic processing for measuring the position of the layer structure of the vascular wall, IMT calculation, and image display control of the measurement result.

Figure 2A:
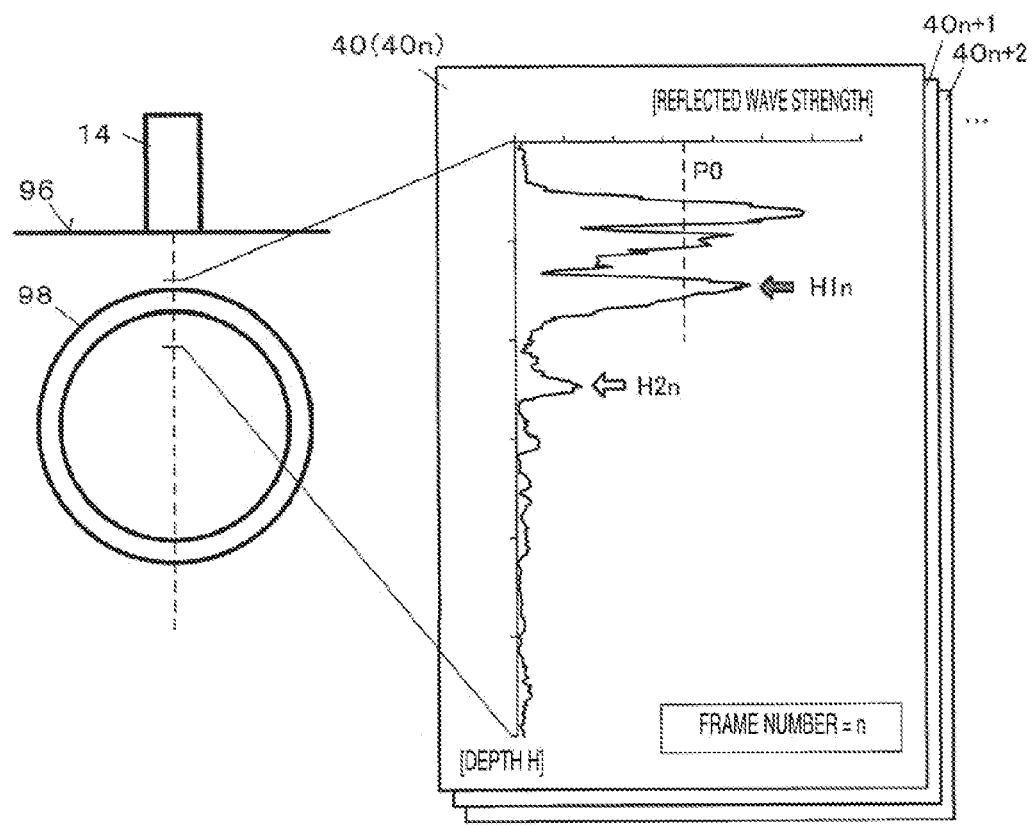
FIGS. 2A and 2B are conceptual diagrams illustrating ultrasound measurement by the ultrasound measurement apparatus.
Figure 2B:
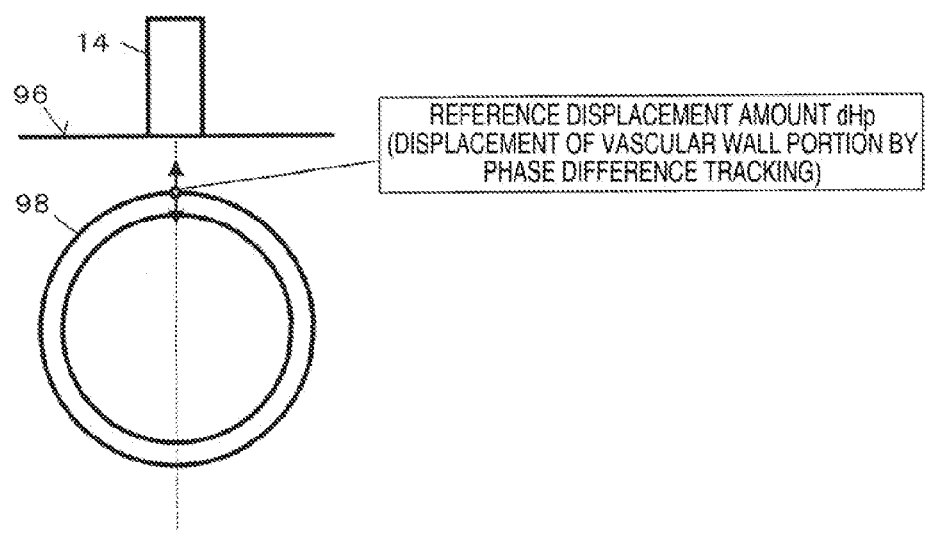

FIGS. 2A and 2B are conceptual diagrams illustrating ultrasound measurement by the ultrasound measurement apparatus 2. In this embodiment, the ultrasound measurement apparatus 2 is configured such that the ultrasound probe 14 which is applied over a skin surface 96 of the subject 90 transmits an ultrasonic pulse toward the blood vessel 98 at a predetermined cycle. Then, a reflected wave from the blood vessel 98 is received and subjected to signal processing, thereby obtaining signal strength data of a reflected wave signal by depth from the skin surface 96, so-called reflected waveform data 40. Reflected waveform data 40 is obtained at every transmission cycle of an ultrasonic wave, that is, at every sampling cycle. Hereinafter, when identifying the sampling cycles, the sampling cycles are called "frames" and are identified with "frame numbers".

As shown in FIG. 2A, the ultrasound measurement apparatus 2 has a function of searching the signal strength peak from reflected waveform data 40 to specify the position of the layer structure of the vascular wall.

A specification method, that is, a specification algorithm can be appropriately prepared. In a first specification method which is prepared by this embodiment, a peak (H1n: n is the frame number) at the deepest position among peaks at which signal strength exceeding predetermined reference signal strength PO is obtained is specified as a first interface, and a peak (H2n: n is the frame number) lower than the first interface searched in a deeper range than the first interface is specified as a second interface. The first interface corresponds to a media-adventitia interface of a blood vessel, and the second interface corresponds to a lumen-intima interface.

A single method or algorithm or a plurality of methods or algorithms of specifying the position of the layer structure of the vascular wall are prepared. The number of specification methods or algorithms can be appropriately set.

As shown in FIG. 2B, the ultrasound measurement apparatus 2 has a function of measuring displacement of the vascular wall with high precision separately from the function of specifying the position of the layer structure of the vascular wall. In this embodiment, this function is realized by phase difference tracking processing.

While various methods for phase difference tracking processing are known, for example, the phase difference tracking processing is realized by the following method. That is, a reflected wave from a displacement measurement target (for example, the outer surface of the vascular wall) is quadrature detected, and the phase θ of a detected waveform when a reflected wave returns from a phase modulation component to a sine wave and a cosine wave with no phase delay is determined. If an ultrasonic pulse is driven at a cycle T0, the minute change velocity v of the target is described by Expression (1) as a value at an intermediate time of two continuous pulses. Then, the minute change velocity v is integrated to calculate minute displacement of the target. The displacement amount obtained by this function is called a "reference displacement amount (dHp)".

$$v(t+T0/2)=-c\{\theta(t+T0)-\theta(t)\}/2\omega 0 T0 \quad (1)$$

Here, ω0=an angular frequency of an ultrasonic wave, and c=sound velocity.

A configuration in which this function is realized by a method different from the phase difference tracking processing may be made. For example, this function may be realized by a displacement calculation method in which an image portion of a part (for example, a part of a B-mode image) of a reflected wave signal is extracted as a template and pattern matching processing is performed, or a method in which, when there is sufficient reflection from the adventitia of the blood vessel 98, an interface portion is traced by a reflected wave signal equal to or greater than a certain threshold value to determine displacement.

Principle of Credibility Evaluation of Interface Specification

As described above, since the thickness of the vascular wall or the wall composition differs for every individual, precision or credibility of specifying the interface of the layer structure of the vascular wall differs depending on a living body to be measured. In other words, credibility is not uniform. Accordingly, the ultrasound measurement apparatus 2 of this embodiment calculates values (evaluation values) for evaluating credibility of the first interface and the second interface using the reference displacement amount dHp based on these values and the displacement amount obtained by the phase difference tracking processing.

Figure 3:
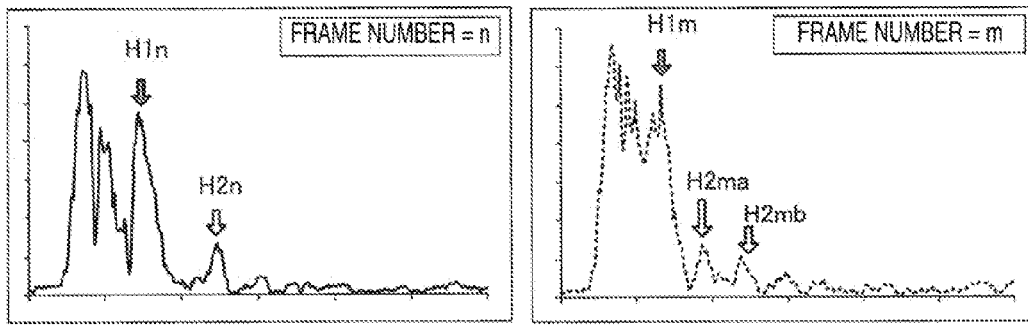
FIG. 3 is a conceptual diagram illustrating the principle of credibility evaluation of interface specification.
Figure 3:
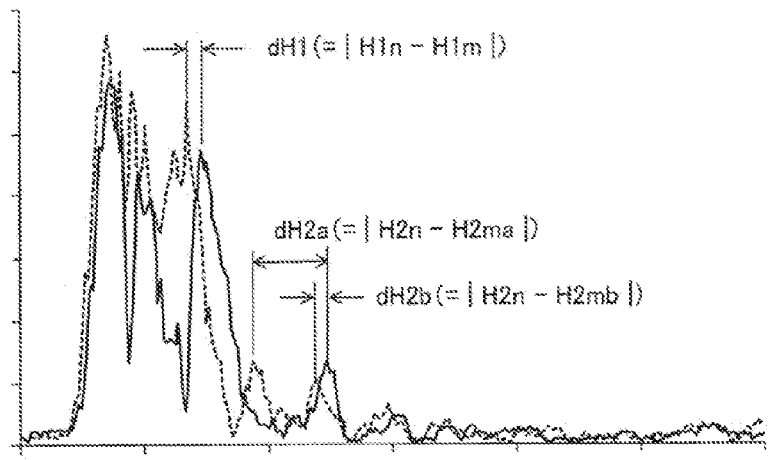
Figure 3:
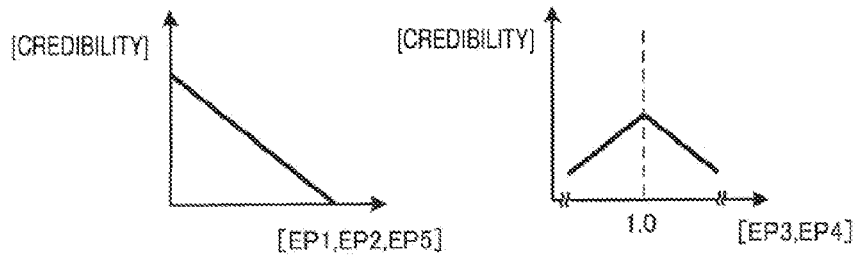

FIG. 3 is a conceptual diagram illustrating the principle of credibility evaluation of interface specification in this embodiment.

For credibility evaluation, at least two pieces of reflected waveform data are used. It is assumed that reflected waveform data 40n of an n-th frame and reflected waveform data 40m of an m-th frame are used. If n≠m, the n-th frame and the m-th frame may be continuous (for example, n=1, m=2) or may be discontinuous (for example, n–1, m=3).

It is assumed that a first interface H1n and a second interface H2n are specified by reflected waveform data 40n of the n-th frame. Then, it is assumed that one first interface H1m and two second interfaces H2ma and H2mb are specified by reflected waveform data 40m of the m-th frame. FIG. 3 shows this case, and credibility of each of the two second interfaces H2ma and H2mb of the m-th frame is evaluated.

In order to determine the evaluation values of credibility, first, the reference displacement amount dHp is calculated between frames to be compared (see FIG. 2B). Then, a first interface displacement amount dH1 and a second interface displacement amount dH2 are calculated between the frames to be compared.

The first interface displacement amount dH1 and the second interface displacement amount dH2 are calculated for each combination of the same type of interfaces specified between different frames. In the example of FIG. 3, since only one first interface H1 is specified for both the n-th frame and the m-th frame, the single first interface displacement amount dH1 is calculated. However, since one second interface H2 is specified in the n-th frame and two second interfaces H2 are specified in the m-th frame, there are the combination of the second interface H2n and the second interface H2ma and the combination of the second interface H2n and the second interface H2mb. Accordingly, the second interface displacement amounts dH2ma and dH2mb for the respective combinations are determined.

Then, since "change in the total thickness of the layer structure accompanying the heartbeat is minute compared to the displacement amount accompanying the heartbeat" and "the difference of change in thickness by layer structure accompanying the heartbeat is minute", first to fifth evaluation values are calculated as an index representing credibility on the basis of the principle that "there is little difference between displacement of the first interface and displacement of the second interface accompanying the heartbeat".

Specifically, the first evaluation value (EP1) is the absolute value of the difference between the reference displacement amount dHp and the first interface displacement amount dH1. The second evaluation value (EP2) is the absolute value of the difference between the reference displacement amount dHp and the second interface displacement amount dH2. The third evaluation value (EP3) is the ratio of the reference displacement amount dHp and the first interface displacement amount dH1l. The fourth evaluation value (EP4) is the ratio of the reference displacement amount dHp and the second interface displacement amount dH2. The fifth evaluation value (EP5) is the absolute value of the difference between the first interface displacement amount dH1 and the second interface displacement amount dH2.

It is considered that, as the first, second, and fifth evaluation values are small, the principle is satisfied. That is, as the evaluation values are small, it can be determined that credibility is high. In regard to the third and fourth evaluation values, when the ratio has the reference displacement amount dHp as a numerator, as the third and fourth evaluation values are close to "1", it can be determined that credibility is high. When credibility is high, this represents that the first interface and the second interface are highly likely to be the position of a layer of the vascular wall. Accordingly, when a predetermined condition that the first, second, and fifth evaluation values are small (for example, equal to or smaller than 0.1 or equal to or smaller than 0.05) is satisfied, or when a predetermined condition that the third and fourth evaluation values are close to "1" (for example, between 0.9 and 1.1 or between 0.95 and 1.05) is satisfied, it is determined that the first interface and the second interface are the position of the layer of the vascular wall.

The ultrasound measurement apparatus 2 of this embodiment outputs the first to fifth evaluation values along with the corresponding first interface H1 or the second interface H2 (for example, displays on the touch panel 4), and provides an operator with the evaluation values as information useful for determination of credibility.

A method (algorithm) of specifying the position of the layer structure of the vascular wall may be evaluated on the basis of these evaluation values. Accordingly, in the ultrasound measurement apparatus 2 in this embodiment, the first interface H1 and the second interface H2 having the highest credibility are selected, and the IMT is calculated and output (for example, displayed on the touch panel 4) on the basis of the selected first interface H1 and second interface H2.

There is no need for calculating all the first to fifth evaluation values, and the first to fifth evaluation values may be appropriately selected depending on the content of biological information to be measured by the ultrasound measurement apparatus 2. For example, a configuration may be made, in which the first evaluation value and the second evaluation value are omitted, the evaluation of credibility of the first interface is omitted, and only credibility of the second interface is evaluated. Of course, the reverse is also possible. If the first interface has high credibility, when determining credibility of the second interface, only the fifth evaluation value may be calculated.

Description of Functional Configuration

Next, a functional configuration for realizing this embodiment will be described.

Figure 4:
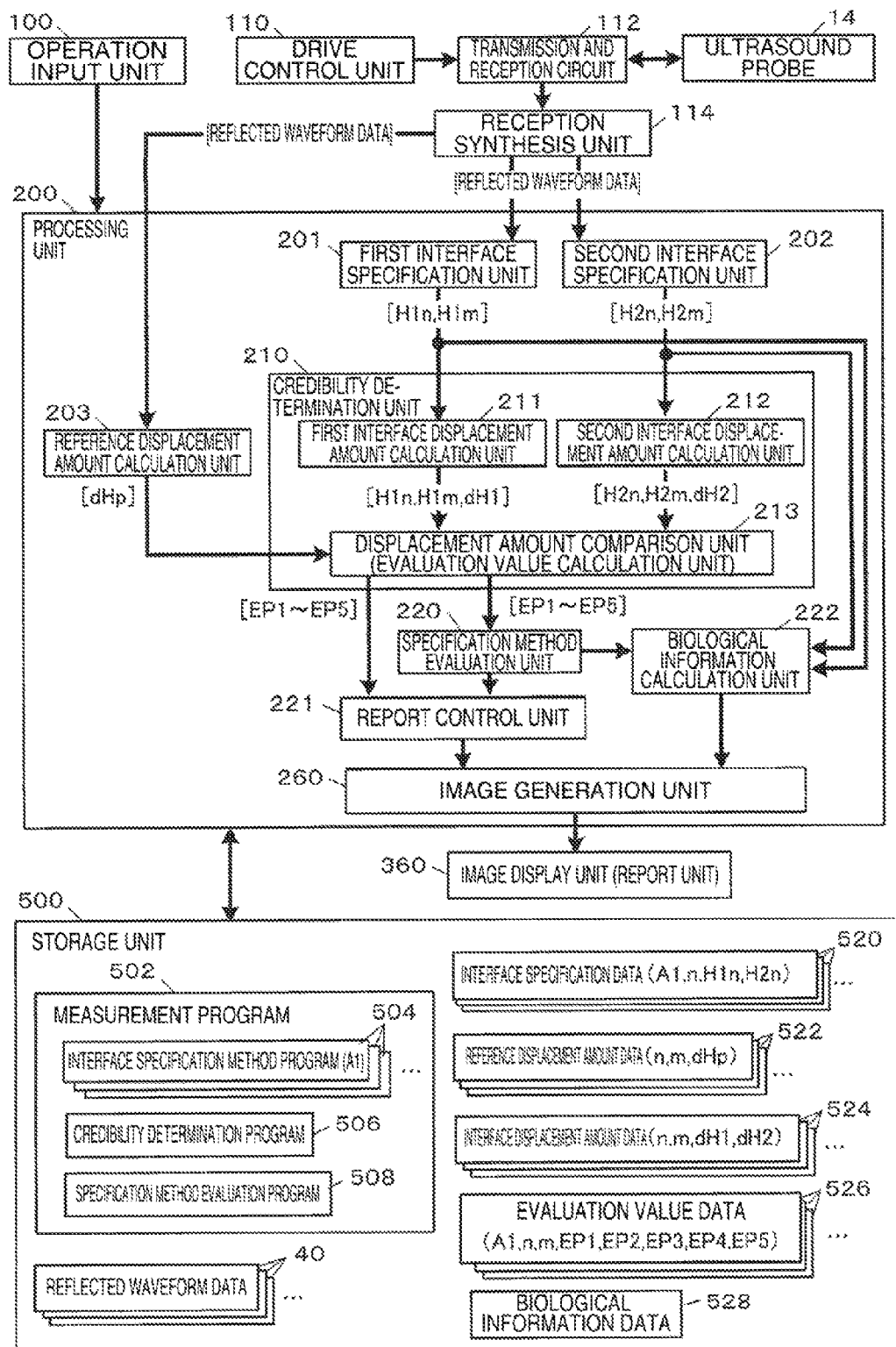
FIG. 4 is a block diagram showing a functional configuration example of the ultrasound measurement apparatus.

FIG. 4 is a block diagram showing a functional configuration example of the ultrasound measurement apparatus 2 of this embodiment.

The ultrasound measurement apparatus 2 includes an operation input unit 100, a drive control unit 110, a transmission and reception circuit 112, a reception synthesis unit 114, a processing unit 200, an image display unit 360, and a storage unit 500.

The operation input unit. 100 receives various operation inputs by the operator and outputs operation input signals according to the operation inputs to the processing unit 200. The operation input unit 100 can be realized by a button switch, a lever switch, a dial switch, a track pad, a mouse, and the like. The touch panel 4 or the keyboard 6 of FIG. 1 corresponds to the operation input unit 100.

The drive control unit 110, the transmission and reception circuit 112, and the reception synthesis unit 114 are realized by a known ultrasound measurement technique, and perform generation or transmission control of an ultrasonic pulse for measurement from the ultrasound probe 14 and amplification or signal processing of a received reflected wave.

Specifically, the drive control unit 110 outputs a transmission control signal for controlling the transmission timing of the ultrasonic pulse from the ultrasound probe 14 to the transmission and reception circuit 112. The transmission and reception circuit 112 generates a pulse voltage in accordance with the transmission control signal from the drive control unit 110 and performs transmission delay processing to adjust the output timing of the pulse voltage to each ultrasound transducer. Amplification or filtering processing of the received reflected wave may be performed, and the result may be output to the reception synthesis unit 114. The reception synthesis unit 114 performs delay processing or the like as necessary to execute processing relating to so-called reception signal focusing, generates reflected waveform data 40, and outputs reflected waveform data 40 to the processing unit 200.

The processing unit 200 is realized by, for example, electronic components including a microprocessor, such as a CPU or a GPU, an ASIC, and an IC memory. Then, input/output control of data between the respective functional units is performed, and various kinds of arithmetic processing relating to measurement are executed on the basis of predetermined programs or data, the operation input signals from the operation input unit 100, and the like. The processing device 30 or the control board 31 of FIG. 1 corresponds to the processing unit 200.

In this embodiment, the processing unit 200 has a first interface specification unit 201, a second interface specification unit 202, a reference displacement amount calculation unit 203, a credibility determination unit 210, a specification method evaluation unit 220, a report control unit 221, a biological information calculation unit 222, and an image generation unit 260.

The first interface specification unit 201 and the second interface specification unit 202 specify the first interface and the second interface in the layer structure of the vascular wall on the basis of reflected waveform data 40. In this embodiment, the first interface and the second interface are specified for each interface specification method (algorithm). Data relating to specification is output to the credibility determination unit 210. Data is stored as interface specification data 520 in the storage unit 500.

Single interface specification data 520 stores identification information (corresponding to "A1" described in an interface specification method program 504 or interface specification data 520, or the like of FIG. 4) representing which interface specification method is used, frame identification information (corresponding to "n" described in interface specification data 520, reference displacement amount data 522, or the like of FIG. 4), and data (interface specification data 520) of the specified first interface H3$n$ and the second interface H2$n$.

The reference displacement amount calculation unit 203 calculates displacement in the ultrasound measurement depth direction of the blood vessel due to the heartbeat, that is, the reference displacement amount dHp. Calculated data is output to the credibility determination unit 210. Data is also stored as reference displacement amount data 522 in the storage unit 500.

Single reference displacement amount data 522 stores two pieces of frame identification information (corresponding to "n" and "m" in FIG. 4) of reflected waveform data 40 used for calculation, and the calculated reference displacement amount dHp.

The credibility determination unit 210 has a first interface displacement amount calculation unit 211, a second interface displacement amount calculation unit 212, and a displacement amount comparison unit 213.

The first interface displacement amount calculation unit 211 calculates the amount of change due to the pulsation at the first interface position, that is, the first interface displacement amount dH1$l$ on the basis of data of the first interface determined by two different pieces of reflected waveform data 40$n$ and 40$m$ (see FIG. 3), and outputs the first interface displacement amount dH1 to the displacement amount comparison unit 213. Similarly, the second interface displacement amount calculation unit 212 calculates the amount of change due to the pulsation at the second interface position, that is, the second interface displacement amount dH2, and outputs the second interface displacement amount dH2 to the displacement amount comparison unit 213.

The calculated first interface displacement amount dH1 and second interface displacement amount dE2 are associated with frame identification information of compared reflected waveform data, and are stored as interface displacement amount data 524 in the storage unit 500.

The displacement amount comparison unit 213 calculates the first evaluation value EP1 to the fifth evaluation value EP5 as an index for determining credibility of the specified first interface H1 and second interface H2 on the basis of the reference displacement amount dHp, the first interface displacement amount dH1, and the second interface displacement amount dH2, and outputs the first evaluation value EP1 to the fifth evaluation value EP5 to the specification method evaluation unit 220. The calculated first evaluation value EP1 to fifth evaluation value EP5 are associated with identification information of a specification method which specifies the first interface H1 and the second interface H2 as a basis of calculation or frame identification information of compared reflected waveform data 40, and are stored as evaluation value data 526 in the storage unit 500.

The specification method evaluation unit 220 evaluates the specification method (in other words, refers to "position detection method" which detects the interface position) which specifies the first interface H1 and the second interface H2. Then, identification information of a specification method suitable for calculation of biological information is output to the biological information calculation unit 222. The evaluation result is output to the image generation unit 260.

Specifically, the specification method evaluation unit 220 determines whether or not a predetermined condition that at least one (for example, the second evaluation value (EP2) related to the lumen-intima interface which is comparatively hard to detect) of the first evaluation value to the fifth evaluation value has high credibility is satisfied. That is, when a predetermined condition that the amount of change of the position specified as the lumen-intima interface is close to the amount of change of the position specified as the position of the media-adventitia interface is satisfied, it is determined that the position specified as the lumen-intima interface correctly specifies the position of the layer of the vascular wall. Then, identification information of a specification method which satisfies the predetermined condition, that is, is evaluated to have high credibility is output to the biological information calculation unit 222.

The report control unit 221 performs control to report the determination result by the credibility determination unit 210. Specifically, the identification information of the specification method and the first evaluation value to the fifth evaluation value of this method corresponding to the determination result are acquired from the credibility determination unit 210. The identification information of the specification method which is evaluated to have high credibility is acquired from the specification method evaluation unit 220. Then, control is performed such that the first evaluation value to the fifth evaluation value by specification method are displayed in association with the result regarding whether or not high credibility is evaluated in an order of the evaluation value of credibility. Instead of display, report output, such as sound output or output of a predetermined notification signal, may be used.

The biological information calculation unit 222 calculates biological information (in this embodiment, the IMT) to be measured by the ultrasound measurement apparatus 2, and outputs the calculation result to the image generation unit 260. The biological information is stored in biological information data 528 of the storage unit 500. Specifically, the distance between the first interface H1 (media-adventitia interface) and the second interface H2 (lumen-intima interface) corresponding to the identification information of the specification method obtained from the specification method evaluation unit 220 is calculated. The calculation result is output to the image generation unit 260.

The image generation unit 260 performs image display control as one of the output forms of the measurement result in this embodiment. Specifically, an image is generated which displays the frame identification information referenced in the interface specification, reflected waveform data 40, the IMT, and information (for example, display in which the first interface H1, the second interface H2, the reference displacement amount dHp, the first evaluation values EP1 to the fifth evaluation value EP5, and the result regarding whether or not high credibility is evaluated are arranged in identification information of the specification method in an ascending order of the evaluation values) corresponding to the report of the determination result by the credibility determination unit 210. Then, a signal for displaying this image is output to the image display unit 360. Accordingly, the image generation unit 260 also has a function as a report unit which reports the determination result of the credibility determination unit 210.

The image display unit 360 is a device which displays an image. The touch panel 4 of FIG. 1 corresponds to the image display unit 360.

The storage unit 500 is realized by a storage medium, such as an IC memory, a hard disk, or an optical disc, and stores various programs or various kinds of data, such as data in the calculation process of the processing unit 200. In the FIG. 1, the storage medium 33 which is mounted on the control board 31 of the processing device 30 corresponds to the storage unit 500. Note that the connection of the processing unit 200 and the storage unit 500 is not limited to connection by an internal bus circuit in the apparatus, and may be realized by a communication line, such as a LAN (Local Area Network) or Internet. In this case, the storage unit 500 may be realized by an external storage device different from the ultrasound measurement apparatus 2.

The storage unit 500 of this embodiment stores a measurement program 502, reflected waveform data 40, interface specification data 520, reference displacement amount data 522, interface displacement amount data 524, evaluation value data 526, and biological information data 528.

The measurement program 502 is a program for realizing the function of the processing unit 200.

For example, if a configuration in which the first interface specification unit 201 and the second interface specification unit 202 are realized by arithmetic processing of the CPU 32 or the like, that is, a configuration in which the first interface specification unit 201 and the second interface specification unit 202 are realized by software is made, an interface specification method program 504 for each method interface specification is included. If a configuration in which the credibility determination unit 210 is realized by software is made, a credibility determination program 506 for causing a computer to realize the function of the credibility determination unit 210 is included. Similarly, if a configuration in which the specification method evaluation unit 220 is realized by software is made, a specification method evaluation program 508 for realizing the function of the specification method evaluation unit 220 is included. Of course, if a configuration in which the functions of the respective units are realized by hardware, such as an electronic circuit, is made, a corresponding program may be omitted.

In addition, it is assumed that counters necessary for various kinds of clocking, flags, various kinds of data necessary for phase tracking control, and the like are appropriately stored in the storage unit 500.

Description of Flow of Processing

Next, the operation of the ultrasound measurement apparatus 2 will be described.

Figure 5:
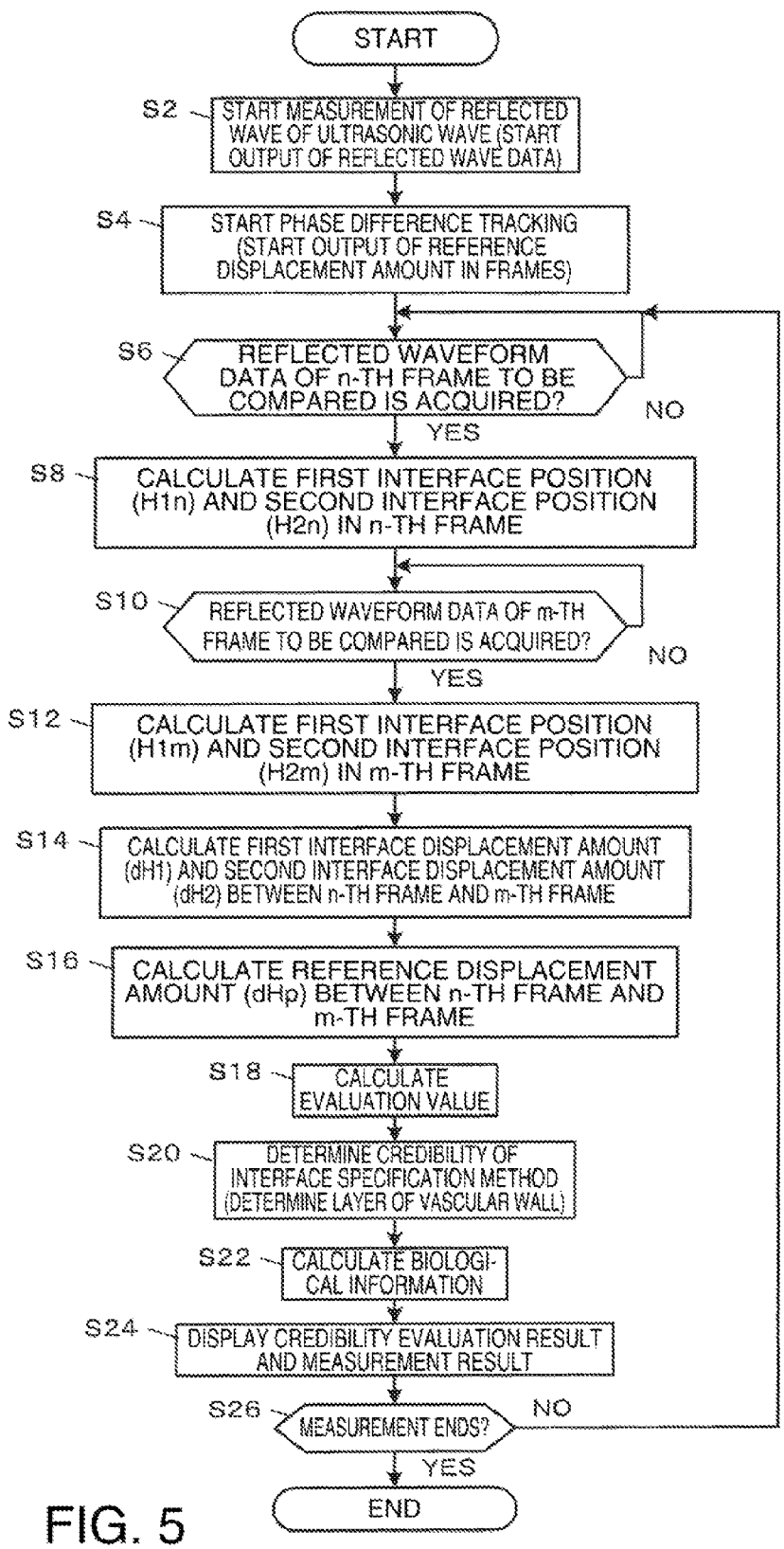
FIG. 5 is a flowchart illustrating the flow of main processing in the ultrasound measurement apparatus.

FIG. 5 is a flowchart illustrating the flow of main processing in the ultrasound measurement apparatus 2 of this embodiment. First, the processing unit 200 of the ultrasound measurement apparatus 2 starts transmission and reception of an ultrasonic pulse for measurement and processing on a reception signal, and generates reflected waveform data 40 at every predetermined cycle to start measurement (Step S2). The phase difference tracking processing starts to start calculation and output of the reference displacement amount dHp in frames (Step S4).

Next, it is determined whether or not reflected waveform data of the n-th frame to be compared for interface position specification can be acquired (Step S6). Here, if n is, for example, a multiple of 10 and m is n+1, the processing of Steps S18 to S24 can be executed in ten frames. However, a method of setting n and m is arbitrary, and if the interval of the processing of Steps S18 to S24 is widened, n should be a multiple of a greater number. If reflected waveform data of the n-th frame can be acquired (YES of Step S6), the processing unit 200 specifies the first interface (HLn) and the second interface (H2n) in the n-th frame (Step S5).

Then, if reflected waveform data of the m-th frame to be compared for interface position specification can be acquired (YES of Step S10), the processing unit 200 specifies the first interface (H1m) and the second interface (H2m) in the m-th frame (Step S12).

Next, the first interface displacement amount (dH1) and the second interface displacement amount (dH2) between the n-th frame and the m-th frame are calculated (Step S14), and the reference displacement amount dHp between the n-th frame and the m-th frame is calculated (Step S16).

Next, the processing unit 200 calculates the first evaluation value to the fifth evaluation value (Step S18), determines credibility for each interface specification method on the basis of the calculated evaluation values, and decides a specification method having the highest credibility and an interface having higher credibility from the first interface and the second interface specified by this method (Step S20). This means that the layer of the vascular wall is determined. Here, the specification method having the highest credibility is decided among specification methods in which credibility satisfies a predetermined condition. The predetermined condition is determined as a condition that the amount of change of the position specified as the lumen-intima interface is close to the amount of change of the position specified as the position of the media-adventitia interface. For example, a condition that the first, second, and fifth evaluation values are equal to or smaller than 0.1 and the third and fourth evaluation values are in a range of 0.9 to 1.1 is determined.

Then, biological information (in this embodiment, the IMT) is calculated on the basis of the determined first interface and second interfaces having the highest credibility (Step S22), and the first interface or the second interface used in calculation, the first evaluation value to the fifth evaluation value, and reflected waveform data 40 are displayed on the touch panel. 4 along with the biological information (Step S24).

Until a measurement end operation is input (NO of Step S26), Steps S6 to S24 are repeatedly executed. Then, if the measurement end operation is input (YES of Step S26), a sequence of processing ends.

According to this embodiment, it becomes possible to determine credibility by calculating the evaluation values for determining credibility in specifying the position of the layer structure (for example, the interface of the layer structure) of the vascular wall on the basis of the reflected wave signal of the ultrasonic wave irradiated onto the blood vessel. It is also possible to determine credibility of the specification method of specifying the position of the layer structure using the evaluation values. Furthermore, the position of the layer structure for use in calculation of biological information is decided on the basis of the evaluation values, thereby increasing measurement precision.

An embodiment to which the invention can be applied is not limited to the foregoing embodiments, and additions, omissions, and alterations of the constituent elements may be appropriately made.

For example, in the foregoing embodiments, although a configuration in which the two positions of the media-adventitia interface and the lumen-intima interface are specified has been described, the number of specified positions of the layer structure may be one or three or more. For example, when the number of specified positions is three or more, for example, the position of the outer surface of the vascular wall can be added to the specified positions. In this case, an interface specification unit and an interface displacement amount calculation unit should be increased.

The format of reflected waveform data can be appropriately set. Various data formats, such as so-called A mode, B mode, and M mode in ultrasound measurement, can be appropriately used.

The entire disclosure of Japanese Patent Application No. 2013-119570, filed Jun. 6, 2013, is expressly incorporated by reference herein.

What is claimed is:

1. An ultrasound measurement apparatus comprising:
a processor having a memory containing algorithms disposed thereon, the algorithms containing the following units:
a first specification unit which specifies the position of a first interface in a layer structure of a vascular wall of a blood vessel on the basis of a reflected wave signal of an ultrasonic wave irradiated onto the blood vessel;
a second specification unit which specifies the position of a second interface in the layer structure of the vascular wall of the blood vessel on the basis of the reflected wave signal; and
a determination unit which determines that both or one of the position specified by the first specification unit and the position specified by the second specification unit is a layer of the vascular wall of the blood vessel on the basis of a comparison between a first interface displacement amount and a second interface displacement amount, the comparison generating:
a first evaluation value being an absolute value of a difference between a reference displacement amount and the first interface displacement amount,
a second evaluation value being an absolute value of a difference between the reference displacement amount and the second interface displacement amount,
a third evaluation value being a ratio of the reference displacement amount and the first interface displacement amount,
a fourth evaluation value being a ratio of the reference amount and the second interface displacement amount, and
a fifth evaluation value being an absolute value of the difference between the first interface displacement amount and the second interface displacement amount,
wherein when the first, second and fifth evaluation values are smaller than 0.1, the determination unit determines with high confidence that the first and second interfaces are the position of the layer of the vascular wall,
wherein, based upon the determination by the determination unit, the ultrasound measurement apparatus measures an intima media thickness of the blood vessel, and displays, on a display unit, the intima media thickness of the blood vessel.

2. The ultrasound measurement apparatus according to claim 1,
wherein the first interface is an interface at which the signal strength of the reflected wave signal appears to be higher than the second interface, and
the determination unit determines that the position specified by the second specification unit is a layer of the vascular wall of the blood vessel when the amount of change of the position specified by the second specification unit is close to the amount of change of the position specified by the first specification unit.

3. The ultrasound measurement apparatus according to claim 2,
wherein the first specification unit specifies the position of a media-adventitia interface of the blood vessel as the position of the first interface, and
the second specification unit specifies the position of a lumen-intima interface of the blood vessel as the position of the second interface.

4. The ultrasound measurement apparatus according to claim 1,
wherein the first specification unit specifies the position of a media-adventitia interface of an anterior wall portion of the blood vessel and the position of a media-adventitia interface of a posterior wall portion of the blood vessel as the position of the first interface,
the second specification unit specifies the position of a lumen-intima interface of an anterior wall portion of the blood vessel and the position of a lumen-intima interface of a posterior wall portion of the blood vessel as the position of the second interface, and
the determination unit calculates the amount of change of the outer diameter of the blood vessel based on the position of the first interface as the amount of change of the position specified by the first specification unit, calculates the amount of change of the inner diameter of the blood vessel based on the position of the second interface as the amount of change of the position specified by the second specification unit, and determines that the position specified by the second specification unit is a layer of the vascular wall of the blood vessel when the amount of change of the position specified by the second specification unit is close to the amount of change of the position specified by the first specification unit.

5. An ultrasound measurement method comprising:
executing first specification processing for specifying the position of a first interface in a layer structure of a vascular wall of a blood vessel on the basis of a reflected wave signal of an ultrasonic wave irradiated onto the blood vessel;
executing second specification processing for specifying the position of a second interface in the layer structure of the vascular wall of the blood vessel on the basis of the reflected wave signal; and
determining that both or one of the position specified by the first specification processing and the position specified by the second specification processing is a layer of the vascular wall of the blood vessel on the basis of a comparison between a first interface displacement amount and a second interface displacement amount, the comparison generating a first evaluation value being an absolute value of a difference between a reference displacement amount and the first interface displacement amount, a second evaluation value being an absolute value of a difference between the reference displacement amount and the second interface displacement amount, a third evaluation value being a ratio of the reference displacement amount and the first interface displacement amount, a fourth evaluation value being a ratio of the reference amount and the second interface displacement amount, and
a fifth evaluation value being an absolute value of the difference between the first interface displacement amount and the second interface displacement amount,
wherein when the first, second and fifth evaluation values are smaller than 0.1, determining with high confidence that the first and second interfaces are the position of the layer of the vascular wall;
based upon the determining that both or one of the position specified by the first specification processing and the position specified by the second specification processing is a layer of the vascular wall of the blood vessel, measuring an intima media thickness of the blood vessel; and
displaying the intima media thickness of the blood vessel.

* * * * *